United States Patent [19]

Jones, Jr.

[11] Patent Number: 5,430,197
[45] Date of Patent: Jul. 4, 1995

[54] RECOVERY OF ALCOHOL FROM HYDROCARBON STREAMS

[75] Inventor: Edward M. Jones, Jr., Pasadena, Tex.

[73] Assignee: Chemica Research & Licensing Company, Pasadena, Tex.

[21] Appl. No.: 199,801

[22] Filed: Feb. 22, 1994

[51] Int. Cl.⁶ .................. C07C 41/06; C07C 43/04; C07C 29/36; C07C 29/80
[52] U.S. Cl. .................. 568/697; 568/913; 568/918
[58] Field of Search .................. 568/913, 697

[56] References Cited

U.S. PATENT DOCUMENTS

| | | | |
|---|---|---|---|
| 2,081,721 | 5/1937 | Van Dijck et al. | 568/918 |
| 3,393,527 | 7/1968 | Swenson et al. | 568/918 |
| 4,198,530 | 9/1980 | Wentzheimer et al. | 568/697 |
| 4,324,924 | 4/1982 | Torck et al. | 568/697 |
| 4,447,668 | 5/1984 | Smith et al. | 585/639 |
| 4,490,563 | 12/1984 | Pool et al. | 568/697 |
| 4,664,675 | 5/1987 | Torck et al. | 568/697 |
| 4,827,045 | 5/1985 | Harendi et al. | 568/697 |
| 4,918,243 | 4/1990 | Smith et al. | 568/697 |
| 5,122,236 | 6/1992 | Smith et al. | 568/697 |
| 5,354,912 | 10/1994 | Hwan et al. | 568/697 |

FOREIGN PATENT DOCUMENTS 156510 1/1952 Australia .................. 568/918

*Primary Examiner*—Joseph E. Evans
*Attorney, Agent, or Firm*—Kenneth H. Johnson

[57] ABSTRACT

Excess alcohol, e.g. methanol contained in a $C_4$-$C_6$ hydrocarbon stream is removed in process using less water and energy than a conventional water wash by subjecting the stream to a first single stage water wash with 2 to 10 wt % water based on the hydrocarbon where most of the alcohol is removed and then washing the raffinate having reduced methanol therefrom subjected to multistage water wash to remove the remainder of the alcohol.

16 Claims, 1 Drawing Sheet

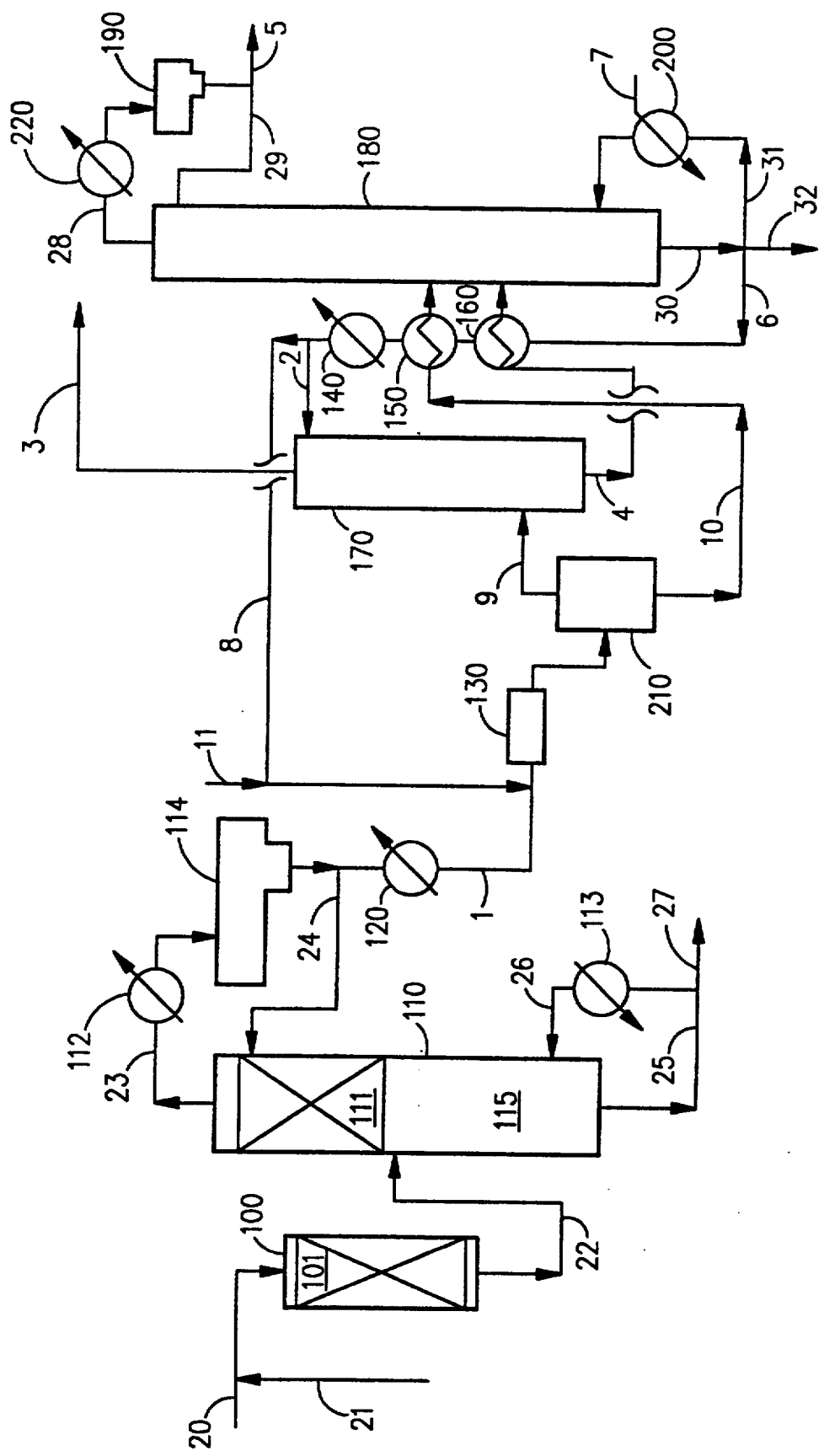

RECOVERY OF ALCOHOL FROM HYDROCARBON STREAMS

BACKGROUND OF THE INVENTION

1. Field of the Invention

The present invention relates to a process for recovering alcohol from admixtures with hydrocarbons.

2. Related Information

Since the Clean Air Act Amendments of 1990 refiners have searched for ways to introduce oxygen into gasoline to produce cleaner burning reformulated fuels. In addition to methyl tertiary butyl ether (MTBE), other suitable ethers for this purpose are tertiary amyl methyl ether (TAME) and ethyl tertiary butyl ether (ETBE). The ethers are produced by the reaction of an alcohol and an olefin using liquid phase reactors, reactive distillation reactors and various combinations.

One highly successful system using concurrent reaction and separation of the reactants from the reaction products by fractional distillation (called catalytic distillation) has been practiced for some time. The process is variously described in U.S. Pat. No. 4,232,177; 4,307,254; 4,336,407; 4,504,687; 4,987,807; and 5,118,873 all commonly assigned herewith.

Briefly, in a catalytic distillation etherification the alcohol and isoolefin are fed to a distillation column reactor having a distillation reaction zone containing a suitable catalyst, such as an acid cation exchange resin, in the form of catalytic distillation structure, and also having a distillation zone containing inert distillation structure. In a preferred embodiment in the etherification of isobutene and/or isoamylenes the olefin and an excess of alcohol, e.g. methanol are first fed to a straight pass reactor wherein most of the olefin is reacted to form the corresponding ether, methyl tertiary butyl ether (MTBE) or tertiary amyl methyl ether (TAME). One type of straight pass reactor is operated at a given pressure such that the reaction mixture is at the boiling point, thereby removing the exothermic heat of reaction by vaporization of the mixture. The described straight pass reactor and process are described more completely in U.S. Pat. No. 4,950,803 which is hereby incorporated by reference.

The effluent from the straight pass reactor is then fed to the distillation column reactor wherein the remainder of the iC$_4$= or iC$_5$='s are converted to the ether and the methanol is separated from the ether, which is withdrawn as bottoms. The C$_4$ or C$_5$ olefin feed stream generally contains only about 10 to 60 percent olefin, the remainder being inerts which are removed in the overheads from the distillation column reactor.

As noted above, in the etherification of olefins with an alcohol, there is preferably an excess of the alcohol available in the reactor. This means that there is an excess of alcohol, e.g. methanol, in the reaction distillation zone of the distillation column reactor. In the distillation column reactor the methanol forms a minimum boiling azeotrope with the unreacted hydrocarbons. If the net methanol flow into the column is higher than the azeotrope, the methanol concentration will increase until alcohol leaves with the bottoms product.

The methanol feed rate is thus best controlled to produce the highest methanol concentration within the catalyst bed while preventing methanol leaving with the bottoms. This results in close to the azeotropic concentration. The methanol must be separated from the hydrocarbons so that the hydrocarbons can be used for gasoline blending and to conserve methanol. The separation is usually achieved by washing the hydrocarbon/methanol mixture with water. The methanol is preferentially absorbed in the water phase, and the water phase is subsequently fractionated to separate the methanol.

The azeotropic concentration of methanol with the unreacted C$_4$'s in the MTBE is only about 4%. The separation is thus relatively easy. However, when the methanol is near to 12% as in the case of C$_5$'s, the separation requires much more water and more theoretical stages in the standard countercurrent contacting mode used. The azeotropes of the unreacted hydrocarbons with other alcohols vary similarly.

SUMMARY OF THE INVENTION

Briefly, the present invention is an improvement in the process of separating alcohol from hydrocarbons, comprising contacting a mixture of alcohol and hydrocarbons with a first water steam and mixing the two vigorously to intimately contact the mixture and the water in a first stage, allowing the water and hydrocarbon to separate into a hydrocarbon phase and a first water phase, removing the hydrocarbon phase, contacting the hydrocarbon phase with a second water steam in multistage water extraction to form a second water phase, recovering the hydrocarbon phase having a substantial reduction in alcohol, and distilling said water phases to recover alcohol.

The present process will operate with any ratio of hydrocarbon/alcohol; however, in the preferred embodiments it will be at or below the azeotropic mixture. As noted above when the alcohol in a catalytic distillation etherification exceeds the azeotrope the excess goes out the bottoms.

The hydrocarbons are preferably C$_4$–C$_6$ and may be the unreacted portion of the overheads from an etherification. The overheads generally comprise alkanes, some normal olefins and possibly some unreacted isoolefin.

In the initial contact of wash water and hydrocarbon/alcohol, one must add enough water to exceed the solubility in the hydrocarbon/alcohol mixture and thereby form a second phase, generally the ratio of water: hydrocarbon/alcohol is in the range of 1:100 to 1:10, preferably 1:50 to 1:20. The amount of alcohol removed from the hydrocarbon stream is a function of water employed; however, in the first stage, usually a single stage contacting the extraction is limited by the equilibrium distribution of the alcohol between the hydrocarbon and the aqueous phases. Generally, from 50 to 95% of the alcohol is extracted in this step. In the single stage extraction the water and hydrocarbons are allowed to phase out and the phases are conveniently separated by decanting. The hydrocarbon stream is subjected to a multistage extraction in the conventional manner where substantially all of the residual alcohol is removed. A few parts per million may remain and are within the specification for gasoline.

The water from the decanter and from the multistage extraction may be combined and distilled to recover the alcohol, which may be recycled to the feed to the etherification; or because the two water phase streams may differ in composition, it may be preferable to feed them to the distillation step separately.

The alcohols are preferably C$_1$ to C$_6$ monohydric alcohols, including methanol, ethanol isopropanol, butanol, tertiary butanol, pentanol and hexanol. Methanol and ethanol are of particular interest because they and certain of their ethers are currently approved as gasoline additives.

In a preferred embodiment the invention relates to a process wherein methanol is reacted with isoamylenes to produce tertiary amyl methyl ether (TAME) and the unreacted methanol and unreacted $C_5$'s are separated by washing with water.

BRIEF DESCRIPTION OF THE DRAWING

The FIGURE is a simplified flow diagram of a TAME process utilizing the dual water wash system of the present invention.

DESCRIPTION OF THE PREFERRED EMBODIMENTS

U.S. Pat. Nos. 5,003,124 and 4,950,803 disclose a liquid phase process for the etherification of $C_4$ and $C_5$ isoolefins with $C_1$ to $C_6$ alcohols in a boiling point fixed bed reactor that is controlled at a pressure to maintain the reaction mixture at its boiling point which may be directly attached to a catalytic distillation reactor.

Although the present invention is described with particular regard to a catalytic distillation, the separation process is suitable to treat any overhead from a distillation or a reactor effluent product where the stream contains hydrocarbons and alcohol.

For example, the reaction product from the boiling point reactor described above may be recovered and fractionated to recover a hydrocarbon/alcohol overhead. Similarly the product from any of the prior art etherifications may be used to provide the hydrocarbon/alcohol feed for the present process.

The catalytic distillation process employs a catalyst system (see U.S. Pat. Nos. 4,215,011 and 4,302,356) which provides for both reaction and distillation concurrently in the same reactor, at least in part within the catalyst system. The method involved is briefly described as one where concurrent reaction and distillation occur in combination reactor-distillation structures which are described in several U.S. Pat. namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

For example, in this system and procedure, methanol and the isoamylene containing $C_5$ stream (or the stream from the boiling point reactor which contains ether, some unreacted isoolefin and methanol) are continuously fed to the reactor/distillation column where they are contacted in the catalytic distillation structure. The methanol preferentially reacts with isoamylene, forming TAME which is heavier than the $C_5$ components of the feed and the methanol, hence it drops in the column to form the bottoms. Concurrently, the unreacted $C_5$'s (e.g. n-pentane, n-pentenes) are lighter and form an overhead.

Catalysts preferred for the etherification process are cation exchangers, which contain sulfonic acid groups, and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles from 0.15 mm up to about 1 mm may be employed.

The resin catalyst is loaded into the fixed bed reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred. The catalytic distillation structure when loaded into the column constitutes a distillation reaction zone.

A preferred embodiment of the present invention comprises a process for the production of tertiary amyl methyl ether comprising the steps of:

(a) feeding a first stream containing $C_5$ hydrocarbons including isoamylenes to a fixed bed straight pass reactor containing an acid cation exchange resin catalyst;

(b) feeding a second stream containing methanol to said fixed bed straight pass reactor whereby a portion of said isoamylenes is reacted with a portion of said isoamylenes is reacted with a portion of said methanol to produce a third stream containing tertiary amyl methyl ether, unreacted methanol, unreacted isoamylenes and unreacted $C_5$'s;

(c) feeding said third stream to a distillation column reactor containing a second fixed bed acid cation exchange resin in the form of a catalytic distillation structure wherein a substantial portion of said unreacted isoamylenes is reacted with methanol to form additional tertiary amyl methyl ether while concurrently separating by fractional distillation unreacted methanol from tertiary amyl methyl ether, said tertiary amyl methyl ether being removed from said distillation column reactor as bottoms and said unreacted methanol along with any unreacted $C_5$'s are removed overheads;

(d) condensing said overheads and collecting said condensed overheads in a receiver;

(e) returning a portion of said condensed overheads to said distillation column reactor as reflux;

(f) contacting the remaining portion of said condensed overheads containing unreacted $C_5$'s and methanol with a first water stream and vigorously mixing said first water stream and unreacted $C_5$'s and methanol to produce a first extract and a first raffinate having a reduced methanol content;

(g) feeding said first raffinate to a multistage water contacting step wherein substantially all of the methanol contained therein is removed to produce a second raffinate which is substantially methanol free and a second extract consisting essentially of methanol and water; and (h) feeding said first and second extracts to a distillation column wherein the methanol and water are separated.

The first water wash step is a gross separation wherein about 65% of the methanol contained the methanol/C5 mixture is removed. Since there is less methanol in the first raffinate, less water is required in the second multistage water wash. This reduces the number of stages required and the amount of energy needed for the separation. In the drawing some conventional items, such as valves have been omitted, however their location and selective use to carry out the functions as described are readily apparent to those in the art.

Referring now to the FIGURE there is shown a simplified flow diagram of a TAME process utilizing the present invention. Methanol is fed via line 20 and a mixed C5 stream is fed via line 21 to a fixed bed single pass reactor 100 containing a bed 101 of acid ion exchange resin catalyst where a portion of the isoamylenes contained in the mixed C5 stream is reacted with methanol to form TAME. The effluent from the reactor 100 is withdrawn via line 22 and contains unreacted methanol, unreacted C5's and TAME. The effluent is fed via line 22 to a distillation column reactor 110 which contains a fixed bed 111 of acid ion exchange resin catalyst in the form of catalytic distillation structure as described above in the upper portion. The fixed bed containing the catalytic distillation structure is denominated the distillation reaction zone. The lower portion 115 of the column 110 contains standard inert distillation structure such as inert packing, sieve trays, bubble cap trays or the like, and is denominated the distillation zone. The TAME in the feed to column 110 is separated out in the lower portion 115 of the column and the unreacted methanol and C5's are boiled up into the distillation reaction zone where the majority of the unreacted isoamylenes react with methanol to form additional TAME which is removed as bottoms via 25 along with the TAME formed in reactor 100. A portion of the bottoms may be circulated through reboiler 113 and line 26 to provide any heat required in the column 110 and the balance recovered as TAME product via line 27.

Any unreacted methanol and C5's are taken overhead along with any other lighter inerts via line 23. Due to the methanol/C5 azeotrope, the amount of methanol in the overheads is about 12.5%. The condensible material in the overheads is condensed in condenser 112 and is collected in receiver 114. The liquid from the receiver is withdrawn and a portion returned to the distillation column reactor 110 as reflux via line 24. The remainder of the liquid is further cooled in heat exchanger 120 and withdrawn via line 1. Water is added to he hydrocarbon-methanol mixture and the stream is passed through static mixer 130 where the water and hydrocarbon-methanol mixture are intimately mixed. The mixed stream from the mixer 130 is then passed to decanter 210 where the water and hydrocarbon phases are allowed to separate. Because of the properties of the C5 hydrocarbon stream, about 65% of the methanol in the hydrocarbon-methanol mixture is preferentially extracted by the water and is carried away by the water phase in line 10 to the methanol/water distillation column 180. A first raffinate, much reduced in methanol content, is removed as the hydrocarbon phase via line 9 and is fed to a conventional multistage contractor 170 where the first raffinate is contacted with additional water to remove essentially all of the remaining methanol.

The second raffinate, essentially methanol free, is removed from the contactor 170 via line 3 and may be sent on to gasoline blending or further processing. The methanol/water is removed from the contactor 170 via line 4 and is also passed on to the methanol/water distillation column 180. The methanol is taken from column 180 as overheads via line 28 and condensed by condenser 220 and collected in receiver 190. A portion of the condensed methanol is returned to the column 180 as reflux via line 29 and the remainder usually recycled (not shown) via line 5 to the feed to the first reactor 100. Water is removed as bottoms via line 30 and a portion recycled via line 31 through reboiler 200. Heat as required is provided for the distillation by steam via line 7. A selective purge line 32 is provided to prevent undesirable contaminant build-up in the recycle water. The remainder of the recovered water is passed via line 6 to heat exchange with both feeds in exchangers 160 and 150 and further cooling in exchanger 140 and recycled via line 2 to the contactor 170. A portion of the recovered water is recycled to the static mixer by combination with the overheads from the distillation column reactor via line 8. In a conventional process all of this stream would have gone back to the contactor 170.

In a conventional process for methanol recovery the first mixer and decanter are not used. However, as shown in TABLE I attached, the conventional method results in considerably more water being required and thus more steam for the reboiler 200 in the methanol/water column than in utilizing the present invention. The conventional process does not have streams 8, 9 or 10. Hence in a conventional process overhead 1 goes directly to contactor 170 and requires 75% more water than the present process. Thus, the present process requires a smaller distillation column and 30% less energy for treating the same stream for methanol recovery than the conventional approach.

Similar benefits can be obtained for other hydrocarbon streams and alcohols than those of the example. The relative solubility of the alcohol in the hydrocarbon stream and water will determine the useful range of materials. $C_4$–$C_8$ hydrocarbon streams, either narrow cuts or mixtures and alcohols, primarily monohydric, of one to six carbon atoms may be separated with the described benefits of the present invention.

TABLE I

| Stream No. | 1 | 2 | 3 | 4 | 5 | 6 | 7 | 8 | 9 | 10 |
|---|---|---|---|---|---|---|---|---|---|---|
| Component, lbs/hr | | | | | | | | | | |
| Hydrocarbon | | | | | | | | | | |
| Invention | 70,000 | — | 70,000 | — | — | — | — | — | 70,000 | — |
| Conventional | 70,000 | — | 70,000 | — | — | — | — | — | — | — |
| Methanol | | | | | | | | | | |
| Invention | 10,000 | — | — | 1,137 | 10,000 | — | — | — | 1,137 | 8,863 |
| Conventional | 10,000 | — | — | 10,000 | 10,000 | — | — | — | — | — |
| Water | | | | | | | | | | |
| Invention | — | 4,548 | — | 4,548 | — | 9,548 | 12,900 | 5,000 | — | 5,000 |

TABLE I-continued

| Stream No. | 1 | 2 | 3 | 4 | 5 | 6 | 7 | 8 | 9 | 10 |
|---|---|---|---|---|---|---|---|---|---|---|
| Conventional Total | — | 40,000 | — | 40,000 | — | 40,000 | 19,500 | — | — | — |
| Invention | 80,000 | 4,548 | 70,000 | 5,685 | 10,000 | 9,548 | 12,900 | 5,000 | 71,137 | 13,863 |
| Conventional | 80,000 | 40,000 | 70,000 | 50,000 | 10,000 | 40,000 | 19,500 | — | — | — |

The invention claimed is:

1. In a process of separating alcohol from hydrocarbons comprising contacting a mixture of alcohol and hydrocarbons with water to extract said alcohol from said hydrocarbons into said water and distillation of the water/alcohol to separate said water and alcohol wherein the improvement comprises intimately mixing a first water stream and said alcohol/hydrocarbon in a first stage allowing said water and hydrocarbon to separate into a hydrocarbon phase and a first water phase, removing the hydrocarbon phase contacting said hydrocarbon phase with a second water stream in a multistage extraction to form a second water phase, recovering the hydrocarbon phase having a substantial reduction in alcohol and distilling the water phases to recover an alcohol fraction and a water fraction.

2. The process according to claim 1 wherein said water phases are distilled together.

3. The process according to claim 1 wherein said alcohol is present in said alcohol/hydrocarbon mixture in an amount not exceeding the azeotrope of said alcohol and hydrocarbon.

4. The process according to claim 1 wherein the ratio of the first water stream to said alcohol/hydrocarbon mixture is in the range of 1:100 to 1:10.

5. The process according to claim 1 wherein said hydrocarbon comprise $C_4$ to $C_6$ hydrocarbon.

6. The process according to claim 1 wherein said alcohol comprise $C_1$ to $C_6$ alcohol.

7. The process according to claim 6 wherein said alcohol comprises methanol and said hydrocarbons comprise $C_5$ hydrocarbons.

8. The process according to claim 1 wherein the first stage is a single stage.

9. In a process for the production of tertiary amyl methyl ether wherein methanol is reacted with isoamylenes contained in a stream of $C_5$ hydrocarbons, the tertiary amyl methyl ether is separated from unreacted methanol and $C_5$ hydrocarbons to yield a methanol/$C_5$ hydrocarbon mixture, and the unreacted methanol and $C_5$ hydrocarbons are separated by a multistage water wash, the improvement comprising subjecting the methanol/$C_5$ hydrocarbon mixture to a first single stage contact with water and subsequent separation prior to the water wash.

10. The process according to claim 9 wherein the concentration of methanol in said methanol/$C_5$ hydrocarbon mixture is about 12%.

11. The process according to claim 10 wherein the concentration of methanol in the effluent from said first single stage contact with water and fed to said multistage water wash is less than 5%.

12. The process according to claim 11 wherein the concentration of methanol in said effluent is about 1.5%.

13. A process for the production of tertiary amyl methyl ether comprising the steps of:
   (a) feeding a first stream containing $C_5$ hydrocarbons including isoamylenes to a fixed bed straight pass reactor containing an acid cation exchange resin catalyst;
   (b) feeding a second stream containing methanol to said fixed bed straight pass reactor whereby a portion of said isoamylenes is reacted with a portion of said methanol to produce a third stream containing tertiary amyl methyl ether, unreacted methanol, unreacted isoamylenes and unreacted $C_5$'s;
   (c) feeding said third stream to a distillation column reactor containing a second fixed bed acid cation exchange resin in the form of a catalytic distillation structure wherein a substantial portion of said unreacted isoamylenes is reacted with methanol to form additional tertiary amyl methyl ether while concurrently separating by fractional distillation unreacted methanol from tertiary amyl methyl ether, said tertiary amyl methyl ether being removed from said distillation column reactor as bottoms and said unreacted methanol along with any unreacted $C_5$'s are removed overheads;
   (d) condensing said overheads and collecting said condensed overheads in a receiver;
   (e) returning a portion of said condensed overheads to said distillation column reactor as reflux;
   (f) contacting the remaining portion of said condensed overheads containing unreacted $C_5$'s and methanol with a first water stream and vigorously mixing said first water stream and unreacted $C_5$'s and methanol to produce a first extract and a first raffinate having a reduced methanol content;
   (g) feeding said first raffinate to a multistage water contacting step wherein substantially all of the methanol contained therein is removed to produce a second raffinate which is substantially methanol free and a second extract consisting essentially of methanol and water; and
   (h) feeding said first and second extracts to a distillation column wherein the methanol and water are separated.

14. The process according to claim 13 further comprising the steps of:
   (i) recycling said separated methanol from step (h) to said fixed bed straight pass reactor of step (b); and
   (j) recycling a portion of said separated water from step (h) to step (f) and the remaining portion of said separated water from step (h) to step (g).

15. The process according to claim 13 wherein the methanol concentration of said condensed overheads is about 12%.

16. The process according to claim 15 wherein the methanol concentration of said first raffinate is about 1.5%.

* * * * *